US008815206B2

(12) United States Patent
Suzuki et al.

(10) Patent No.: US 8,815,206 B2
(45) Date of Patent: Aug. 26, 2014

(54) ALUMINUM HYDROXIDE GEL PARTICLE AND PRODUCTION METHOD THEREOF

(71) Applicant: Kyowa Chemical Industry Co., Ltd., Kagawa (JP)

(72) Inventors: Takafumi Suzuki, Kagawa (JP); Shinjiro Tamagawa, Kagawa (JP)

(73) Assignee: Kyowa Chemical Industry Co., Ltd., Kanagawa (JP)

( * ) Notice: Subject to any disclaimer, the term of this patent is extended or adjusted under 35 U.S.C. 154(b) by 0 days.

(21) Appl. No.: 13/759,447

(22) Filed: Feb. 5, 2013

(65) Prior Publication Data

US 2013/0145965 A1    Jun. 13, 2013

Related U.S. Application Data

(62) Division of application No. 13/059,857, filed as application No. PCT/JP2009/064321 on Aug. 7, 2009, now Pat. No. 8,524,192.

(30) Foreign Application Priority Data

Aug. 19, 2008  (JP) ................................. 2008-210844

(51) Int. Cl.
   *C01F 7/00*   (2006.01)
   *C09C 1/40*   (2006.01)
   *C01F 7/34*   (2006.01)
   *C01F 7/02*   (2006.01)
   *A61K 33/08*  (2006.01)

(52) U.S. Cl.
   CPC . *C09C 1/407* (2013.01); *C01F 7/34* (2013.01); *C01P 2006/80* (2013.01); *C01F 7/02* (2013.01); *A61K 33/08* (2013.01)
   USPC ........................................................ 423/629

(58) Field of Classification Search
   None
   See application file for complete search history.

(56) References Cited

U.S. PATENT DOCUMENTS

| 2,474,888 A | * | 7/1949 | Connolly ...................... 502/235 |
| 2,773,839 A | | 12/1956 | Stover et al. |
| 3,395,221 A | | 7/1968 | Snyder |
| 3,499,963 A | | 3/1970 | Rubino |
| 4,297,325 A | | 10/1981 | Scherzer et al. |
| 4,849,190 A | | 7/1989 | De Castro Morshbacker et al. |
| 2003/0190281 A1 | | 10/2003 | Kudermann et al. |
| 2006/0165801 A1 | | 7/2006 | Ishii |

FOREIGN PATENT DOCUMENTS

| JP | 1-24731 | 5/1989 |
| JP | 10-109030 | 4/1998 |
| JP | 11-278829 | 10/1999 |
| JP | 2008-19158 | 1/2008 |

OTHER PUBLICATIONS

Translation of Japan 11-278829, Oct. 1999.*
International Search Report issued Mar. 17, 2011 in corresponding International Application No. PCT/JP2009/064321.
English translation of the International Preliminary Report on Patentability issued on Mar. 17, 2011, in corresponding International Application No. PCT/JP2009/064321.
Korean Office Action issued Jun. 7, 2012 in corresponding Korean Application No. 10-2011-7003233, with English translation.
European Search Report issued Oct. 30, 2012 in corresponding European Application No. 09 80 8234.
Japanese Office Action issued May 16, 2012 in corresponding Japanese Patent Application No. 2010-525680, with English translation.
Chinese Office Action issued Oct. 30, 2012 in corresponding Chinese Patent Application No. 200980132025, with English translation.
T. Fujita et al., "Formation of Activated Alumina from Polyhydroxoaluminum Gels Having Difference [OH/Al] Ratios", Journal of the Ceramic Society of Japan, vol. 106, No. 10, pp. 1017-1022, 1998, with partial English translation.
L. Zhang et al., "Synthesis of Nano-Alumina Hydroxide Sol Using Sol-gel Method", Acta Phys. -Chim Sin., vol. 23, No. 5, pp. 728-732, 2007, with partial English translation.
X. Chaofen et al., "Synthesis of lanthanum aluminate by ethylene diamine tetraacetic acid gel route", J. Huazhong Univ. of Sci. & Tech. (Nature Science Edition), vol. 33, No. 1, 2005, with partial English translation.

* cited by examiner

*Primary Examiner* — Steven Bos
(74) *Attorney, Agent, or Firm* — Wenderoth, Lind & Ponack, L.L.P.

(57) ABSTRACT

An aluminum hydroxide gel particle having high purity and extremely high acid reactivity and a production method thereof.
The aluminum hydroxide gel particle has an iron (Fe) content of 1 to 10 ppm.

2 Claims, No Drawings

ALUMINUM HYDROXIDE GEL PARTICLE AND PRODUCTION METHOD THEREOF

TECHNICAL FIELD

The present invention relates to a high-purity aluminum hydroxide gel particle which is useful as a raw material for high-performance optical lenses or as an electric or electronic material and a production method thereof.

BACKGROUND ART

Aluminum hydroxide gel particles are used as a pharmaceutical antacid, a flame retardant, or an electric or electronic material in a wide variety of fields. However, since it has a Fe content close to 200 ppm, there is a limit to the use of the particle as an electric or electronic material which is required to have high purity.

To produce aluminum hydroxide, there is known a method in which a sodium aluminate solution is used as a starting material. For example, Patent Document 1 proposes a method for producing aluminum hydroxide through the following steps. That is, an oxidant is caused to act on a sodium aluminate aqueous solution to decompose organic matter contained in sodium aluminate. Thereafter, seed crystal aluminum hydroxide is added to precipitate a small amount of aluminum hydroxide (Fe as an impurity contained in sodium aluminate as a raw material is adsorbed at the time of precipitating aluminum hydroxide) so as to remove it. A chelating agent is then added to the sodium aluminate solution from which the impurity has been removed, and a carbon dioxide gas is introduced to precipitate aluminum hydroxide which is then washed in an aqueous solution containing the chelating agent to produce aluminum hydroxide.

However, the aluminum hydroxide obtained by this method is crystalline aluminum hydroxide which differs from an aluminum hydroxide gel (amorphous aluminum hydroxide) which is targeted by the present invention. This document proposes that a complex should be formed by adding a chelating agent to sodium aluminate so as to reduce the Fe content of the obtained aluminum hydroxide. However, as the sodium aluminate aqueous solution is alkaline (pH of not less than 10), it is easily assumed that Fe is not existent as an ion but as a hydroxide (super fine particle). Since objective substance must be an ion in a complex formation using chelating agent, aluminum hydroxide having a low Fe content cannot be produced by this method. Further, a complex cannot be produced by the method of washing with water containing the chelating agent, since Fe to be targeted is existent as a hydroxide.

Patent Document 2 proposes a method in which an aqueous solution of supersaturated sodium aluminate having a content of dissolved $Na_2O$ of not less than 100 g/l and a Fe content in the liquid of not more than 0.4 mg/l and a molar ratio of dissolved $Na_2O$ to dissolved $Al_2O_3$ of 1.6 to 2.0 is used as a raw material solution. That is, Patent Document 2 discloses a method for obtaining aluminum hydroxide by controlling the temperature of the raw material, the content of the dissolved $Na_2O$ and the above molar ratio, limiting the BET specific surface area of seed crystal aluminum hydroxide to 1 to 7 $m^2/g$ and Fe to be contained in the seed crystal aluminum hydroxide and further controlling the supersaturation of the raw material solution. However, even aluminum hydroxide obtained by this method is also crystalline aluminum hydroxide and not an aluminum hydroxide gel particle (amorphous aluminum hydroxide) which is targeted by the inventors of the present invention.
(Patent Document 1) JP-A 2008-19158
(Patent Document 2) JP-A 11-278829

DISCLOSURE OF THE INVENTION

It is an object of the present invention to provide an aluminum hydroxide gel particle which has high purity and extremely high acid reactivity and a production method thereof.

The inventors of the present invention have conducted intensive studies to produce an aluminum hydroxide gel particle having high purity, especially a low content of the iron element (Fe). As a result, they have found that the content of the iron element (Fe) in the aluminum hydroxide gel particle can be reduced very efficiently when a chelating agent is added to a soluble aluminum salt aqueous solution such as aluminum sulfate as a raw material to form an iron (Fe) complex. Further, they have also found that it is effective to carry out a reaction between an aqueous solution of an alkali metal or ammonium carbonate and a soluble aluminum salt aqueous solution in a specific molar ratio of $CO_3$ to $Al_2O_3$ at a specific temperature range. The present invention has been accomplished based on these findings.

That is, the present invention is an aluminum hydroxide gel particle having a content of the iron element (Fe) of 1 to 10 ppm.

The present invention is also a method of producing an aluminum hydroxide gel particle, comprising the steps of:
(1) adding a chelating agent to a soluble aluminum salt aqueous solution to form a complex;
(2) reacting an aqueous solution of an alkali metal or ammonium carbonate with a soluble aluminum salt aqueous solution containing the obtained complex in a molar ratio ($CO_3/Al_2O_3$) of the carbonate ion contained in the carbonate to aluminum oxide contained in the soluble aluminum salt of 3.0 to 4.5 at a temperature of 10 to 40° C.;
(3) carrying out the solid-liquid separation of the obtained reaction product to obtain a cake;
(4) bringing the obtained cake into contact with an aqueous solution of at least one ion exchange agent selected from the group consisting of an inorganic acid and a water-soluble aluminum salt; and
(5) drying the cake.

BEST MODE FOR CARRYING OUT THE INVENTION

The aluminum hydroxide gel particle of the present invention can be produced through the following steps:
(1) adding a chelating agent to a soluble aluminum salt aqueous solution to form a complex (complex forming step);
(2) reacting an aqueous solution of an alkali metal or ammonium carbonate with a soluble aluminum salt aqueous solution containing the obtained complex in a molar ratio ($CO_3/Al_2O_3$) of the carbonate ion contained in the carbonate to aluminum oxide contained in the soluble aluminum salt of 3.0 to 4.5 at a temperature of 10 to 40° C. (reaction step);
(3) carrying out the solid-liquid separation of the obtained reaction product to obtain a cake (solid-liquid separation step);
(4) bringing the obtained cake into contact with an aqueous solution of at least one ion exchange agent selected from the group consisting of an inorganic acid and a water-soluble aluminum salt (ion exchange step); and
(5) drying the cake (drying step).

(Complex Forming Step)

The complex forming step is a step for adding a chelating agent to a soluble aluminum salt aqueous solution to form a complex.

Examples of the soluble aluminum salt include aluminum chloride, aluminum nitrate and aluminum sulfate, out of which aluminum sulfate is most preferred as it is inexpensive.

The iron element (Fe) contained in the aluminum hydroxide gel of the prior art is wholly derived from a soluble aluminum salt which is a raw material thereof. Therefore, Fe contained in this soluble aluminum salt should be subjected to some treatment to prevent it from being contained in the obtained aluminum hydroxide gel. When a chelating agent is added to an aqueous solution of the soluble aluminum salt to form a complex, Fe forming the complex is discharged together with a reaction mother liquid, thereby reducing the Fe content of the obtained aluminum hydroxide gel. The selective formation of a Fe ion complex in the presence of a large amount of the aluminum ion is assumed to be because the pH of the soluble aluminum salt aqueous solution is not more than 2.5, the Fe ion complex is formed at a pH of not more than 2, and an aluminum complex is formed at a pH of not less than 3.

The chelating agent is a salt of ethylenediaminetetraacetic acid. Examples of the salt of ethylenediaminetetraacetic acid include disodium ethylenediaminetetraacetate, trisodium ethylenediaminetetraacetate, tetrasodium ethylenediaminetetraacetate, diammonium ethylenediaminetetraacetate, triammonium ethylenediaminetetraacetate, tetraammonium ethylenediaminetetraacetate, trisodium hydroxyethyl ethylenediaminetriacetate, triammonium hydroxyethyl ethylenediaminetriacetate, disodium dihydroxyethyl ethylenediaminediacetate, diammonium dihydroxyethyl ethylenediaminediacetate, pentasodium diethylenetriaminepentaacetate, pentaammonium diethylenetriaminepentaacetate, hexasodium triethylene tetraminehexaacetate, hexaammonium triethylene tetraminehexaacetate, disodium hydroxyethyliminodiacetate, diammonium hydroxyethyliminodiacetate, tetrasodium nitrilotrimethylenephosphonate, pentasodium nitrilotrimethylenephosphonate, trisodium hydroxyethanediphosphonate and tetrasodium hydroxyethanediphosphonate. Out of these, disodium ethylenediaminetetraacetate, trisodium ethylenediaminetetraacetate and tetrasodium ethylenediaminetetraacetate are preferred. These chelating agents may be used alone or in combination of two or more.

The amount of the chelating agent is 1 to 30 times, preferably 5 to 25 times, more preferably 10 to 20 times the molar amount of the Fe ion contained in the soluble aluminum salt aqueous solution as a raw material. When the amount of the chelating agent is not more than 1 mole based on the Fe ion, the amount of the formed complex is small and the object of the present invention cannot be attained. When the amount of the chelating agent is not less than 30 times the molar amount of the Fe ion, it is costly and economically disadvantageous.

(Reaction Step)

The reaction step is a step for reacting an aqueous solution of an alkali metal or ammonium carbonate with a soluble aluminum salt aqueous solution containing the complex obtained in the complex forming step in a molar ratio ($CO_3/Al_2O_3$) of the carbonate ion contained in the carbonate to aluminum oxide contained in the soluble aluminum salt of 3.0 to 4.5 at a temperature of 10 to 40° C.

Examples of the alkali metal carbonate include potassium carbonate and sodium carbonate, out of which sodium carbonate is most preferred. Ammonium carbonate is also effective.

The reaction can be a batch reaction which is carried out by injecting a predetermined amount of the soluble aluminum salt aqueous solution at a fixed rate while a predetermined amount of the carbonate aqueous solution is injected into a reactor and stirred, or by injecting a predetermined amount of the carbonate aqueous solution at a fixed rate while a predetermined amount of the soluble aluminum salt aqueous solution is injected into the reactor and stirred. Although a continuous reaction may be carried out by injecting the soluble aluminum salt aqueous solution and the alkali carbonate aqueous solution into a reactor equipped with an overflow into which a predetermined amount of water has been injected in a predetermined ratio, a continuous reaction having high productivity (reactivity) is preferred.

The concentration of the carbonate aqueous solution is preferably 0.7 to 2.0 moles/l. The concentration of the soluble aluminum salt aqueous solution is preferably 0.25 to 1.2 moles/l as $Al_2O_3$.

The ratio of the carbonate aqueous solution to the soluble aluminum salt is such that the ratio ($CO_3/Al_2O_3$) of the carbonate ion contained in the carbonate to aluminum oxide contained in the soluble aluminum salt should be 3.0 to 4.5, preferably 3.3 to 3.9.

The reaction temperature is 10 to 40° C., preferably 20 to 30° C. The reaction pH which is controlled by the injection ratio of the carbonate to the soluble aluminum salt is about 6.0 to 7.0.

(Solid-Liquid Separation Step)

The solid-liquid separation step is a step for carrying out the solid-liquid separation of the obtained reaction product to obtain a cake. That is, the solid-liquid separation of the reaction product obtained in the reaction step is carried out to obtain an aluminum hydroxide gel as a cake. The solid-liquid separation may be carried out by an ordinary method such as filtration or centrifugation.

(Ion Exchange Step)

The ion exchange step is a step for bringing the cake obtained in the solid-liquid separation step into contact with an aqueous solution of at least one ion exchange agent selected from the group consisting of an inorganic acid and a water-soluble aluminum salt.

The ion exchange treatment is carried out to substitute the sodium ion adsorbed to the aluminum hydroxide gel by a hydrogen ion or aluminum ion so as to reduce the content of sodium oxide in the aluminum hydroxide gel to not more than 0.1 wt %.

Examples of the inorganic acid include hydrochloric acid, nitric acid and sulfuric acid. Examples of the water-soluble aluminum salt include aluminum sulfate, aluminum nitrate and aluminum chloride. Although sulfuric acid and aluminum sulfate can substitute the sodium ion adsorbed to the aluminum hydroxide gel by a hydrogen ion or aluminum ion, the sulfate ion is strongly adsorbed to the aluminum hydroxide gel and is hardly removed, therefore sulfuric acid and aluminum sulfate are not preferable. Therefore, sulfuric acid and aluminum sulfate are not preferred. Therefore, hydrochloric acid, nitric acid, aluminum chloride and aluminum nitrate are preferred, and hydrochloric acid and aluminum chloride are more preferred from the viewpoint of cost.

Ion exchange can be carried out by letting the cake obtained by solid-liquid separation with a filter press or drum filter pass through an aqueous solution of the above ion exchange agent having a concentration of $1 \times 10^{-3}$ to $1.5 \times 10^{-3}$ mole/l in an amount 70 to 100 times the volume of solid matter (aluminum hydroxide gel). When the concentration of the inorganic acid is lower than $1 \times 10^{-3}$ mole/l, ion exchange efficiency degrades and the amount of the solution must be increased at the same time, which is uneconomical. When the concentration of the inorganic acid is higher than $1.5 \times 10^{-3}$ mole/l, aluminum contained in the cake is dissolved, thereby reducing the yield. The temperature of the solution at the time of ion exchange is not particularly limited but a temperature of 15 to 30° C. suffices.

(Drying Step)

The drying step is a step for drying the cake obtained in the ion exchange step. Examples of the drier include a spray drier, band drier and conductive heat transmission groove type stirring drier. Out of these, a spray drier is most preferred. To spray dry the cake, the cake is dehydrated, re-emulsified and dried after ion exchange.

(Aluminum Hydroxide Gel Particle)

According to the production method of the present invention, an aluminum hydroxide gel particle having an iron (Fe) content of 1 to 10 ppm is obtained. The iron (Fe) content is preferably not more than 5 ppm, more preferably not more than 3 ppm.

According to the production method of the present invention, an aluminum hydroxide gel particle having (1) an iron (Fe) content of 1 to 10 ppm, (2) a sodium oxide content of not more than 0.1 wt % and (3) a 0.1 mole/l hydrochloric acid consumption of not less than 250 ml when measured by an antacid force measurement method specified in the 15$^{th}$ Revision of Japanese Pharmacopoeia is obtained.

The content of sodium oxide ($Na_2O$) is preferably not more than 0.05 wt %, more preferably not more than 0.04 wt %.

The 0.1 mole/l hydrochloric acid consumption is preferably not less than 280 ml, more preferably not less than 300 ml.

EXAMPLES

The following examples are provided for the purpose of further illustrating the present invention but are in no way to be taken as limiting. The characteristic properties of the aluminum sulfate aqueous solution and the sodium carbonate aqueous solution as raw materials and the obtained aluminum hydroxide gel were measured by the following methods.

(1) Aluminum ($Al_2O_3$) contained in the aluminum sulfate aqueous solution was measured by a chelate titration method and the iron element (Fe) was measured by using the SPS1500VR ICP-AES device of Seiko Instrument Inc.

(2) The concentration of carbonic acid ($CO_3$) contained in sodium carbonate was measured in accordance with Japanese Standards of Food Additives.

(3) The iron element (Fe) contained in the aluminum hydroxide gel was measured by using SPS1500VR type ICP-AES device of Seiko Instrument Inc.

Antacid force (hydrochloric acid consumption) was measured in accordance with the method of measuring the antacid force of dried aluminum hydroxide gel of Japanese Pharmacopoeia. That is, 0.2 g of the dried aluminum hydroxide gel was weighed accurately and injected into a stoppered flask, 100 ml of 0.1 mole/l hydrochloric acid was added to the flask accurately, the flask was stoppered tightly, these substances were shaken to be mixed together at 37±2° C. for 1 hour, and the resulting mixture was filtered. 50 ml of the filtrate was weighed accurately and an excessive amount of hydrochloric acid was titrated with a 0.1 moles/l sodium hydroxide solution while they were stirred fully until its pH became 3.5.

Sodium oxide ($Na_2O$) was measured by using the ANA-135 flame photometer of Tokyo Koden Co., Ltd.

Example 1

(Complex Forming Step (1))

An aqueous solution prepared by dissolving 2 g of disodium ethylenediaminetetraacetate (EDTA-2Na) in 200 ml of tap water was added to 1,000 ml of an aluminum sulfate aqueous solution having an $Al_2O_3$ concentration of 1.05 moles/l and a Fe concentration of 15 mg/l and dispersed into the solution under agitation to obtain an aluminum sulfate aqueous solution containing Fe contained in aluminum sulfate as a complex. The molar amount of EDTA-2Na was 20 times the molar amount of Fe contained in the above aluminum sulfate. The $Al_2O_3$ concentration of the obtained aluminum sulfate aqueous solution was 0.874 moles/l.

(Reaction Step)

500 ml of tap water was fed to a 2.2-liter stainless steel reactor equipped with an overflow, the aluminum sulfate aqueous solution prepared in the complex forming step (1) and a 0.76 moles/l sodium carbonate aqueous solution were supplied into the reactor at rates of 14.8 ml/min and 58.5 ml/min at the same time by using a quantitative pump under agitation, respectively, and a reaction was carried out continuously at a temperature of 22 to 24° C. for 65 minutes. The molar ratio ($CO_3/Al_2O_3$) of the sodium carbonate aqueous solution to the sodium sulfate aqueous solution was 3.44.

The reaction pH was always 6.52 to 6.54.

(Solid-Liquid Separation Step)

The obtained reaction suspension was filtered with suction by using a Nutsche, and the cake remaining in the Nutsche was obtained.

(Ion Exchange Step)

Subsequently, 14.5 l of $1 \times 10^{-3}$ moles/l hydrochloric acid was supplied into the Nutsche to remove sodium contained in the cake by ion exchange. The amount of this liquid was about 85 times the calculated value of solid matter.

(Drying Step)

The ion exchanged liquid was re-emulsified to a concentration of 300 g/l in terms of solid matter and dried with a laboratory-scale spray drier to obtain an aluminum hydroxide gel particle. The characteristic properties of the obtained aluminum hydroxide gel particle are shown in Table 1.

Example 2

An aluminum sulfate aqueous solution containing Fe contained in aluminum sulfate as a complex was obtained in the same manner as in the complex forming step (1) of Example 1 except that the amount of EDTA-2Na was changed to 1.5 g (complex forming step (2)). The amount of EDTA-2Na was 15 times the molar amount of Fe contained in aluminum sulfate.

An aluminum hydroxide gel particle was obtained in the same manner as in Example 1 except that the aluminum sulfate aqueous solution used in the reaction was changed to the aluminum sulfate aqueous solution prepared in the above complex forming step (2) and that the inorganic acid aqueous solution used for ion exchange was changed to 14.5 liters of $1 \times 10^{-3}$ moles/l nitric acid. The characteristic properties of the obtained aluminum hydroxide gel particle are shown in Table 1.

Example 3

An aluminum sulfate aqueous solution containing Fe in aluminum sulfate as a complex was obtained in the same manner as in the complex forming step (1) of Example 1 except that the amount of EDTA-2Na was changed to 1 g (complex forming step (3)). The amount of EDTA-2Na was 10 times the molar amount of Fe contained in aluminum sulfate.

An aluminum hydroxide gel particle was obtained in the same manner as in Example 1 except that the aluminum sulfate aqueous solution used in the reaction was changed to the aluminum sulfate aqueous solution prepared in the above complex forming step (3) and that the aqueous solution used for ion exchange was changed to 14.5 liters of a $1 \times 10^{-3}$ moles/l aluminum chloride aqueous solution. The characteristic properties of the obtained aluminum hydroxide gel particle are shown in Table 1.

Example 4

An aqueous solution prepared by dissolving 2.43 g of tetrasodium ethylenediaminetetraacetate (EDTA-4Na) in 200 ml of tap water was added to 1,000 ml of an aluminum sulfate aqueous solution having an $Al_2O_3$ concentration of 1.05 moles/l and an Fe concentration of 15 mg/l and dispersed into the solution under agitation to obtain an aluminum sulfate aqueous solution containing Fe contained in aluminum sulfate as a complex (complex forming step (4)). The amount of EDTA-4Na was 20 times the molar amount of Fe contained in the above aluminum sulfate. The $Al_2O_3$ concentration of the obtained aluminum sulfate aqueous solution was 0.874 moles/l.

An aluminum hydroxide gel particle was obtained in the same manner as in Example 1 except that the aluminum sulfate aqueous solution used in the reaction was changed to the aluminum sulfate aqueous solution prepared in the above complex forming step (4). The characteristic properties of the obtained aluminum hydroxide gel particle are shown in Table 1.

Example 5

An aqueous solution prepared by dissolving 487 mg of disodium ethylenediaminetetraacetate (EDTA-2Na) in 100 ml of tap water was added to 1,000 ml of an aluminum sulfate aqueous solution having an $Al_2O_3$ concentration of 107 g/l and an Fe concentration of 7.3 mg/l and dispersed into the solution under agitation to obtain an aluminum sulfate aqueous solution containing Fe contained in aluminum sulfate as a complex (complex forming step (5)). The amount of EDTA-2Na was 10 times the amount of Fe contained in the above aluminum sulfate. The $Al_2O_3$ concentration of the obtained aluminum sulfate aqueous solution was 0.874 moles/l.

An aluminum hydroxide gel particle was obtained in the same manner as in Example 1 except that the aluminum sulfate aqueous solution used in the reaction was changed to the aluminum sulfate aqueous solution prepared in the above complex forming step (5). The characteristic properties of the obtained aluminum hydroxide gel particle are shown in Table 1.

Comparative Example 1

An aluminum hydroxide gel particle was obtained in the same manner as in Example 1 except that aluminum sulfate was changed to a non-treated aluminum sulfate aqueous solution. The characteristic properties of the obtained aluminum hydroxide gel particle are shown in Table 1.

Comparative Example 2

An aluminum hydroxide gel particle was obtained in the same manner as in Example 5 except that aluminum sulfate was changed to a non-treated aluminum sulfate aqueous solution. The characteristic properties of the obtained aluminum hydroxide gel particle are shown in Table 1.

It is understood from Examples 1 to 5 that when a chelating agent is added to an aluminum sulfate aqueous solution to obtain the Fe ion of the aluminum sulfate aqueous solution as a complex and this complex is discharged as a mother liquid, the content of Fe in the obtained aluminum hydroxide gel can be reduced. It is also understood that, by washing with an inorganic acid or a salt of an inorganic acid, the amount of sodium contained in the obtained aluminum hydroxide gel can be reduced and an aluminum hydroxide gel particle having high purity can be obtained. It is further seen that the aluminum hydroxide gel of the present invention has high reactivity with a low-concentration acid as obvious from its antacid force value.

TABLE 1

| | Fe content (ppm) | $Na_2O$ content (wt %) | Antacid force (mL) |
|---|---|---|---|
| Example 1 | 2.2 | 0.05 | 315 |
| Example 2 | 3.5 | 0.04 | 308 |
| Example 3 | 4.8 | 0.05 | 317 |
| Example 4 | 2.1 | 0.04 | 312 |
| Example 5 | 3.6 | 0.04 | 306 |
| Comparative Example 1 | 102.0 | 0.05 | 315 |
| Comparative Example 2 | 49.0 | 0.04 | 305 |

EFFECT OF THE INVENTION

The difference in characteristic properties between aluminum hydroxide (crystalline) and the aluminum hydroxide gel (amorphous) of the present invention is that aluminum hydroxide has extremely low reactivity with an acid whereas the aluminum hydroxide gel of the present invention has extremely high reactivity with an acid.

When aluminum hydroxide is used as a raw material for producing a high-performance optical lens or as an electric or electronic material, it is often dissolved in an inorganic acid or organic acid and used as a salt. Since aluminum hydroxide has low acid reactivity, the concentration of the acid to be used must be made high and the temperature must be made high. In contrast to this, since the aluminum hydroxide gel of the present invention has extremely high acid reactivity, an inorganic acid or organic acid salt is obtained easily and economically.

The aluminum hydroxide gel particle obtained by the present invention has a Fe content of 1 to 10 ppm. It has a sodium oxide ($Na_2O$) content of not more than 0.1 wt %. Further, it has a 0.1 moles/l hydrochloric acid consumption of not less than 250 ml when measured by Test for Acid-neutralizing Capacity of Gastrointestinal Medicines specified in Japanese Pharmacopoeia Fifteen Edition.

According to the present invention, even when a soluble aluminum salt having a high Fe content is used as a raw material, an aluminum hydroxide gel particle having an Fe content of not more than 10 ppm, a sodium oxide content of not more than 0.1 wt % and a 0.1 moles/l hydrochloric acid consumption of not less than 250 ml when measured by the antacid force measurement method specified in the $15^{th}$ Revision of Japanese Pharmacopoeia can be obtained easily and economically.

INDUSTRIAL APPLICABILITY

The aluminum hydroxide gel particle of the present invention can be used as a raw material for producing high-performance optical lenses and electric and electronic materials.

The invention claimed is:

1. An amorphous aluminum hydroxide gel particle having a Fe content of 1 to 10 ppm.

2. The amorphous aluminum hydroxide gel particle according to claim 1, which has:
   (1) a sodium oxide content of not more than 0.1 wt %, and
   (2) a 0.1 mole/l hydrochloric acid consumption of not less than 250 ml when measured by an antacid force measurement method,
   wherein the method comprises drying the amorphous aluminum hydroxide gel,
   adding 0.2 g of the dried amorphous aluminum hydroxide gel into a flask,
   adding 100 ml of 0.1 mole/l hydrochloric acid to the flask,
   stoppering the flask with a stopper,
   shaking the flask at 37±2°C. for 1 hour,
   filtering a resulting mixture to obtain a filtrate,
   obtaining 50 ml of the filtrate, wherein an excessive amount of the hydrochloric acid is titrated with a 0.1 mole/l sodium hydroxide solution while stirring until pH is 3.5.

* * * * *